(12) United States Patent
Gosakan

(10) Patent No.: US 11,883,315 B2
(45) Date of Patent: Jan. 30, 2024

(54) CONFORMABLE ORTHOSIS

(71) Applicant: Rock Stance, Bangalore (IN)

(72) Inventor: Haripriya Sumana Gosakan, Bangalore (IN)

(73) Assignee: Rock Stance, Bangalore (IN)

( * ) Notice: Subject to any disclaimer, the term of this patent is extended or adjusted under 35 U.S.C. 154(b) by 477 days.

(21) Appl. No.: 17/259,551

(22) PCT Filed: Jul. 12, 2019

(86) PCT No.: PCT/IN2019/050518
§ 371 (c)(1),
(2) Date: Jan. 12, 2021

(87) PCT Pub. No.: WO2020/012508
PCT Pub. Date: Jan. 16, 2020

(65) Prior Publication Data
US 2021/0186736 A1    Jun. 24, 2021

(51) Int. Cl.
*A61F 5/058* (2006.01)
*A61F 5/01* (2006.01)

(52) U.S. Cl.
CPC .. *A61F 5/05858* (2013.01); *A61F 2005/0172* (2013.01)

(58) Field of Classification Search
CPC .......... A61F 5/05858; A61F 2005/0172; A61F 5/058; A61F 5/05841; A61F 5/05; A61F 5/04; A61F 5/01; A61F 5/00; A61F 13/04; A61F 13/041; A61F 13/00
See application file for complete search history.

(56) References Cited

U.S. PATENT DOCUMENTS

2009/0227923 A1* 9/2009 Markus ................. A61F 13/046
602/14
2020/0101190 A1* 4/2020 Zhu ......................... A61L 15/14

FOREIGN PATENT DOCUMENTS

| CN | 106102666 A | * | 11/2016 | ........... A61F 5/0102 |
| CN | 206228482 U | * | 6/2017 | |
| CN | 110269735 A | * | 9/2019 | ............. A61F 5/058 |
| CN | 111166545 A | * | 5/2020 | ............. A61B 90/18 |
| CN | 112190390 A | * | 1/2021 | ......... A61B 5/02438 |

* cited by examiner

*Primary Examiner* — Tarla R Patel
(74) *Attorney, Agent, or Firm* — Yantra Patents LLC; Anand P Narayan

(57) ABSTRACT

A conformable and reconfigurable orthosis is provided. The conformable and reconfigurable orthosis comprises a central core metallic wire resistive heating element, an electrically insulating layer such as glass fiber or nylon fiber, and a structural layer of carbon fiber composites. The conformable and reconfigurable orthosis further comprises a thermal insulation and/or a skin compatible cushioning layer.

5 Claims, 4 Drawing Sheets

CONFORMABLE ORTHOSIS

CROSS-REFERENCE TO RELATED APPLICATIONS

This application is a U.S. National Stage filing under 35 U.S.C. § 371 of International Patent Application No. PCT/IN2019/050518, filed 12 Jul. 2019, which claims priority to and the benefit of provisional patent application titled "Conformable Orthosis", application number 201841026261, filed in the Indian Patent Office on 13 Jul. 2018. The specification of the above referenced patent applications are incorporated herein by reference in their entirety.

BACKGROUND

The apparatus disclosed herein, in general, relates to a medical device, and in particular, relates to a conformable and reconfigurable orthosis. Orthotic supports are dimensionally specific to a patient's body. For example, casts made of plaster of Paris or casts made of existing types of composites cannot be refitted from one patient to another if they differ in size. Ankle and foot orthosis need to snugly fit to the ankle, calf and foot to be effective. Spinal orthosis supports require to confirm to the shape of the spine to provide effective support. Hence, there is an unmet need for orthotic support devices that are conformable to the abutting body part, and that can be reconfigurable in shape.

SUMMARY OF THE INVENTION

The apparatus disclosed herein addresses the above recited unmet need for orthotic support that are conformable and reconfigurable. Advantageously, such a conformable and reconfigurable orthosis can be adjusted in shape to accommodate for body swelling.

DETAILED DESCRIPTION OF THE INVENTION

Figure 1A:
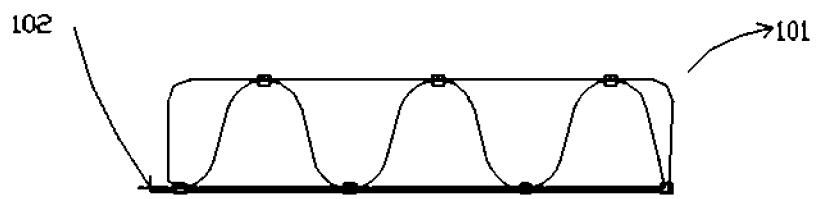
FIG. 1A illustrates a flat grid conformable and reconfigurable orthosis.
Figure 1B:
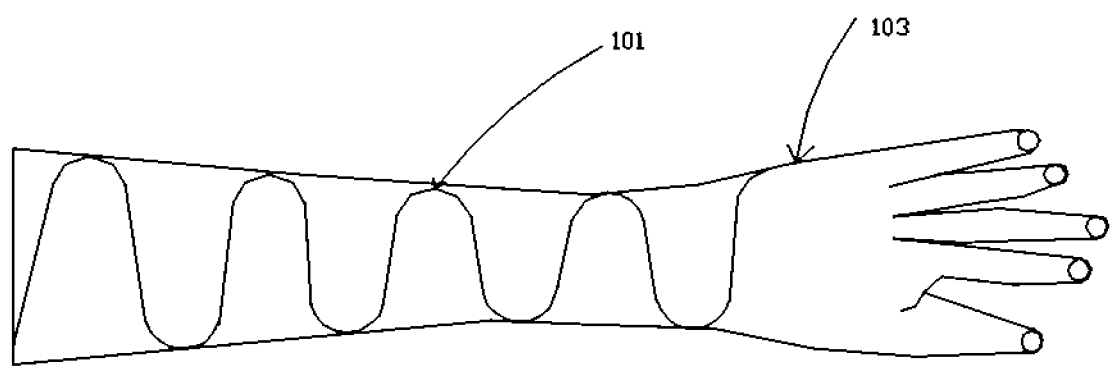
FIG. 1B illustrates the conformable and reconfigurable orthosis wrapped as a three-dimensional support on an arm of a patient.

FIG. 1A illustrates a flat grid conformable and reconfigurable orthosis 101. The grid is composed of rope like sections. By electrically connecting a lead point 102 to a power source, the heat of internal wiring in the conformable and reconfigurable orthosis 101 softens the conformable and reconfigurable orthosis 101 and allows the conformable and reconfigurable orthosis 101 to be easily wrapped on an arm 103 of a patient as exemplarily illustrated in FIG. 1B. FIG. 1B illustrates the conformable and reconfigurable orthosis 101 wrapped as a support on the arm 103 of the patient. After cooling, the shape of the conformable and reconfigurable orthosis 101 sets to the wrapped form. FIG. 1B exemplarily illustrates a wrapping of the conformable and reconfigurable orthosis 101 around the arm 103 of a patient with a hand fracture.

Figure 2:
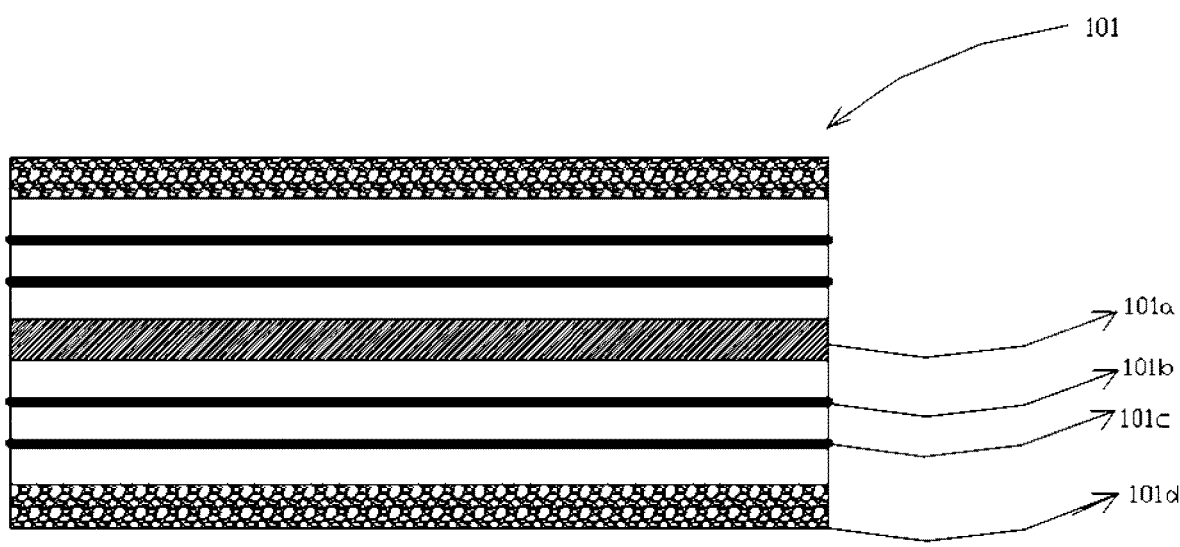
FIG. 2 illustrates an internal structure of the conformable and reconfigurable orthosis.

FIG. 2 illustrates an internal structure of the conformable and reconfigurable orthosis 101. The conformable and reconfigurable orthosis 101 comprises a central core metallic wire resistive heating element 101a, an electrically insulating layer 101b such as glass fiber or nylon fiber, a structural layer 101c of carbon fiber composites, and a thermal insulation and/or a skin compatible cushioning layer 101d. For example, a 0.5 mm diameter nichrome wire core is the electrically resistive central core metallic wire resistive heating element 101a that is configured to reach a maximum temperature of 180° Celsius based on the input current and the maximum set voltage. The electrically insulating layer 101b is a braided glass fiber sleeve. The structural layer 101c is a carbon fiber composite with a glass transition temperature or a thermal deformity temperature less than the temperature to which the central core metallic wire resistive heating element 101a heats the structural layer 101c. The carbon fiber composite comprises carbon fiber in a thermoplastic or thermosetting matrix. In an embodiment, a thermoset resin epoxy is used in the structural layer 101c. The thermal insulation layer 101d is a lightweight and thermally insulating layer, for example, a soft polyester fiber that significantly inhibits transfer heat to the patient's arm 103 exemplarily illustrated in FIG. 1B. FIG. 1B illustrates the conformable and reconfigurable orthosis wrapped as a three-dimensional support on an arm of a patient. Optionally, a thermal insulation cloth may first be laid on the body part, and subsequently removed after the conformable and reconfigurable orthosis 101 has cooled and set into shape.

For example, a thin 2 mm thick insulation cloth was placed on a test mannequin hand. The 0.5 mm diameter electrical nicrome wire was electrically charged to rapidly heat it to 180 C within five seconds. Within another five seconds the carbon fiber structural layer 101c heated upto 180 C and softened. The heated conformable and reconfigurable orthosis 101 was then placed on the insulation above the mannequin hand and then gently pressed to the contour of the mannequin's hand. As the carbon fiber structural layer 101c heated upto 180 C, it came to the consistency of a flexible rope, very little pressure was needed. Within 10 seconds the gentle pressure was released, the structural layer 101c rapidly cooled, and the shape was set for the orthosis. The thermal insulation layer 101d, acted as a partial heat sink and did not allow transfer of heat to the mannequin hand. The temperature on the mannequin hand did not exceed 45 degree celcius even temporarily for 5 seconds. The 2 mm thick insulation cloth acted as a second level of insulation. In many test cases, there was no need for the thick insulation cloth. The insulation cloth was later easily slid and removed from under the set orthosis.

Figure 3:
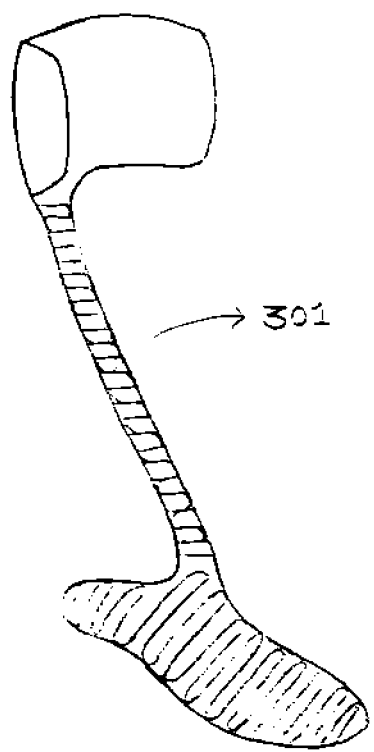
FIG. 3 illustrates the conformable and reconfigurable orthosis used in an ankle and foot orthosis.

FIG. 3 illustrates the conformable and reconfigurable orthosis 101 used in an ankle and foot orthosis. The following conformable members 301 are embedded within the structure of the ankle and foot orthosis: central core metallic wire resistive heating element 101a, an electrically insulating layer 101b such as glass fiber or nylon fiber, a structural layer 101c of carbon fiber composites, and a thermal insulation and/or a skin compatible cushioning layer 101d.

Figures 4A, 4B:
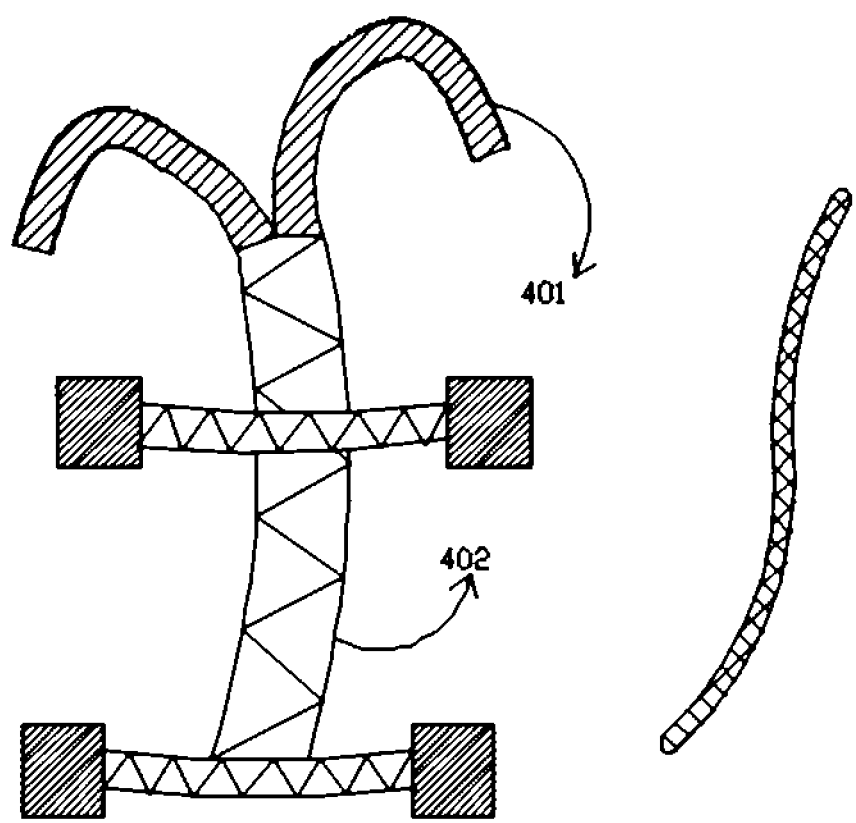
FIG. 4A illustrates a front view of the conformable and reconfigurable orthosis used in a spinal orthosis.
FIG. 4B illustrates a side view of the conformable and reconfigurable orthosis used in a spinal orthosis.

FIG. 4A illustrates a front view of the conformable and reconfigurable orthosis 101 used in a spinal orthosis. FIG. 4B illustrates a side view of the conformable and reconfigurable orthosis 101 used in a spinal orthosis. The following conformable members are embedded within the structure of the spinal orthosis 402: central core metallic wire resistive heating element 101a, an electrically insulating layer 101b such as glass fiber or nylon fiber, a structural layer 101c of carbon fiber composites, and a thermal insulation and/or a skin compatible cushioning layer 101d. The straps 401 hold the spinal orthosis to the body.

The apparatus disclosed herein is applicable for any type of orthotic support, and is not limited to hand orthosis, spinal orthosis and ankle and foot orthosis as exemplified. For example, it can be applied for neck supports, back supports, pelvic supports, wrist supports, shoulder, elbow and knee bracing supports.

The foregoing examples have been provided merely for explanation and are in no way to be construed as limiting of the conformable and reconfigurable orthosis 101 disclosed herein. While the conformable and reconfigurable orthosis 101 has been described with reference to various embodiments, it is understood that the words, which have been used herein, are words of description and illustration, rather than words of limitation. Furthermore, although the conformable and reconfigurable orthosis 101 has been described herein with reference to particular means, materials, and embodiments, the conformable and reconfigurable orthosis 101 is not intended to be limited to the particulars disclosed herein; rather, the conformable and reconfigurable orthosis 101 extends to all functionally equivalent structures, methods and uses, such as are within the scope of the appended claims. While multiple embodiments are disclosed, it will be understood by those skilled in the art, having the benefit of the teachings of this specification, that the conformable and reconfigurable orthosis 101 disclosed herein is capable of modifications and other embodiments may be effected and changes may be made thereto, without departing from the scope and spirit of the conformable and reconfigurable orthosis 101 disclosed herein.

I claim:

1. A conformable and reconfigurable orthosis, comprising:
   a grid comprising rope like sections, wherein said rope like sections comprise:
     a central core resistive heating element that is configured to reach a maximum temperature of 180 degree Celsius;
     an electrically insulating layer;
     a structural layer of carbon fiber composite with a glass transition temperature that is less than said reached temperature of said central core resistive heating element; and
     a thermal insulation layer that acts as a heat sink for cooling said heated central core resistive heating element, thereby setting a shape of said conformable and reconfigurable orthosis, and wherein the thermal insulation layer inhibits heat transfer from said central core to skin of a wearer of said conformable and reconfigurable orthosis; and
   an electrical lead for connecting the conformable and reconfigurable orthosis to a power source.

2. The conformable and reconfigurable orthosis of claim 1, further comprising a cushioning layer abutting the skin.

3. The conformable and reconfigurable orthosis of claim 1, wherein said central core resistive heating element is a metallic wire element.

4. The conformable and reconfigurable orthosis of claim 1, wherein said electrically insulating layer is a fiber glass sleeve.

5. A method of conforming a conformable and reconfigurable orthosis on a body part, comprising the steps of:
   electrically connecting a lead point of said conformable and reconfigurable orthosis to a power source, said conformable and reconfigurable orthosis further comprising:
     a grid composed of rope like sections, wherein said rope like sections comprise:
       a central core resistive heating element that is configured to reach a maximum temperature of 180 degree Celsius;
       an electrically insulating layer;
       a structural layer of carbon fiber composite with a glass transition temperature that is less than said reached temperature of said central core resistive heating element; and
       a thermal insulation layer that acts as a heat sink for cooling said heated central core resistive heating element, and wherein the thermal insulation layer inhibits heat transfer from said central core to skin of a wearer of said conformable and reconfigurable orthosis; and
     an electrical lead for connecting the conformable and reconfigurable orthosis to a power source;
   whereby heat of internal wiring in the conformable and reconfigurable orthosis softens the conformable and reconfigurable orthosis;
   wrapping said softened conformable and reconfigurable orthosis on the body part; and
   cooling and setting into shape said conformable and reconfigurable orthosis.

* * * * *